(12) United States Patent
Smilansky et al.

(10) Patent No.: US 7,454,052 B2
(45) Date of Patent: *Nov. 18, 2008

(54) PIXEL BASED MACHINE FOR PATTERNED WAFERS

(75) Inventors: Zeev Smilansky, Meishar (IL); Sagie Tsadka, Yavne (IL); Zvi Lapidot, Rehovot (IL); Rivi Sherman, Ramat-Hasharon (IL)

(73) Assignee: Applied Materials, Inc., Santa Clara, CA (US)

( * ) Notice: Subject to any disclaimer, the term of this patent is extended or adjusted under 35 U.S.C. 154(b) by 709 days.

This patent is subject to a terminal disclaimer.

(21) Appl. No.: 11/042,509

(22) Filed: Jan. 26, 2005

(65) Prior Publication Data

US 2005/0129303 A1 Jun. 16, 2005

Related U.S. Application Data

(60) Continuation of application No. 10/281,125, filed on Oct. 28, 2002, now abandoned, which is a division of application No. 10/003,347, filed on Dec. 6, 2001, now Pat. No. 7,016,526, which is a division of application No. 09/110,870, filed on Jul. 7, 1998, now Pat. No. 6,366,690.

(51) Int. Cl.
*G06K 9/00* (2006.01)
*H04N 7/18* (2006.01)

(52) U.S. Cl. .......................... 382/149; 348/86; 348/125; 356/237.1

(58) Field of Classification Search ......... 382/141–152; 250/306–311, 223; 348/86–95, 125–134; 700/95–212; 29/833; 438/16; 356/237.1–237.6, 356/426–431; 702/35–40
See application file for complete search history.

(56) References Cited

U.S. PATENT DOCUMENTS 4,000,949 A 1/1977 Watkins (Continued)

FOREIGN PATENT DOCUMENTS

DE 43 21 042 9/1994

(Continued)

OTHER PUBLICATIONS

"Multi-Layer Coated Optics: Guided Wave Coupling and Scattering by Means of Interface Random Roughness"; Elson, J. Opt. Soc. AM. vol. 12, No. 4; Apr. 1995; pp. 729-742.

(Continued)

*Primary Examiner*—Aaron W Carter
(74) *Attorney, Agent, or Firm*—Sughrue Mion PLLC; Patterson & Sheridan LLP

(57) ABSTRACT

A method is provided for the detection of defects on a semiconductor wafer by checking individual pixels on the wafer, collecting the signature of each pixel, defined by the way in which it responds to the light of a scanning beam, and determining whether the signature is that of a faultless pixel or of a pixel that is defective or suspect to be defective. An apparatus is also provided for the determination of such defects, which comprises a stage for supporting a wafer, a laser source generating a beam that is directed onto the wafer, collecting optics and photoelectric sensors for collecting the laser light scattered by the wafer in a number of directions and generating corresponding analog signals, an A/D converter deriving from the signals digital components defining pixel signatures, and selection systems for identifying the signatures of suspect pixels and verifying whether the suspect pixels are indeed defective.

35 Claims, 13 Drawing Sheets

U.S. PATENT DOCUMENTS

| | | |
|---|---|---|
| 4,342,515 A | 8/1982 | Akiba et al. |
| 4,345,312 A | 8/1982 | Yasuye et al. |
| 4,423,331 A | 12/1983 | Koizumi et al. |
| 4,516,833 A | 5/1985 | Fusek |
| 4,532,650 A | 7/1985 | Wihl et al. |
| 4,628,531 A | 12/1986 | Okamoto et al. |
| 4,669,875 A | 6/1987 | Shiba et al. |
| 4,731,855 A | 3/1988 | Suda et al. |
| 4,814,596 A | 3/1989 | Koizumi et al. |
| 5,451,773 A * | 9/1995 | Triner et al. ............ 250/223 B |
| 5,699,447 A | 12/1997 | Alumot et al. |
| 5,801,824 A | 9/1998 | Henley |

FOREIGN PATENT DOCUMENTS

| | | |
|---|---|---|
| JP | 54-101390 | 8/1979 |
| JP | 55-94145 | 7/1980 |
| JP | 56-30630 | 3/1981 |
| JP | 06-242015 | 2/1993 |
| JP | 06-137239 | 6/1994 |
| JP | 08-007103 | 1/1996 |

OTHER PUBLICATIONS

"A New Curve Detection Method: Randomized Hough Transform (RHT)"; Xu et al.; Pattern Recognition Letters 11 (1990) pp. 331-338.

"Autoranging/Autofocus: A Survey of Systems", Part 3; Wolpert; Photonics Spectra Sep. 1987, pp. 133-141.

* cited by examiner

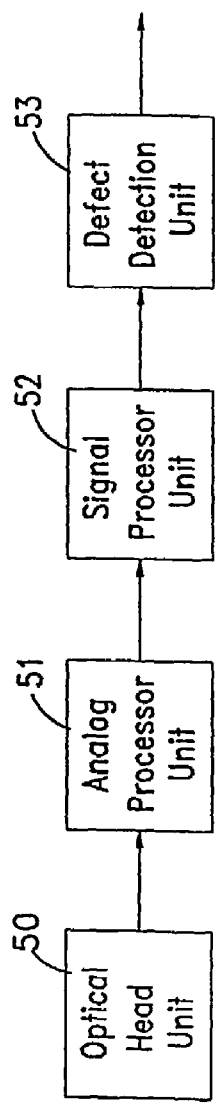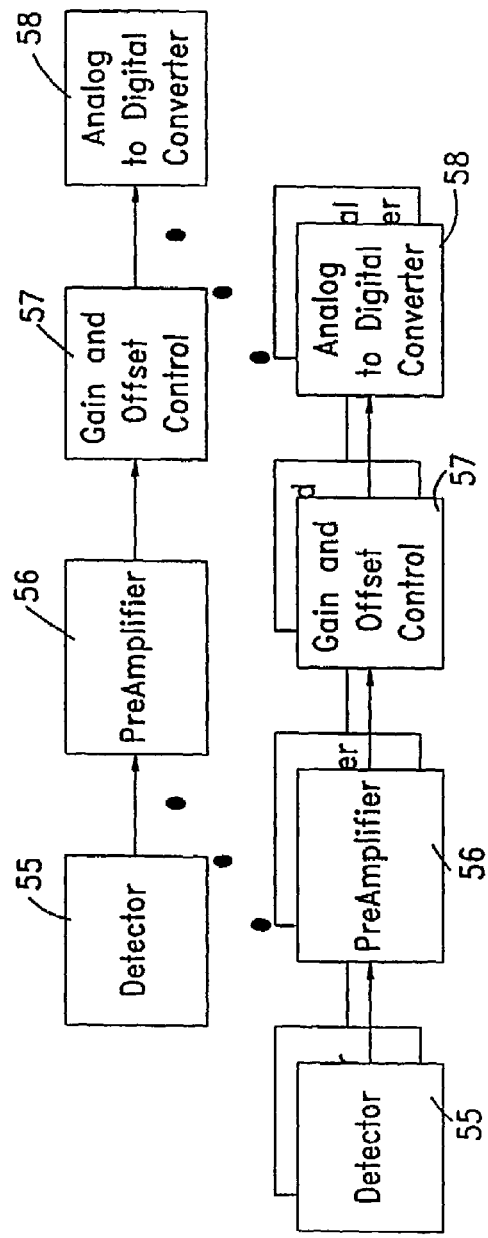

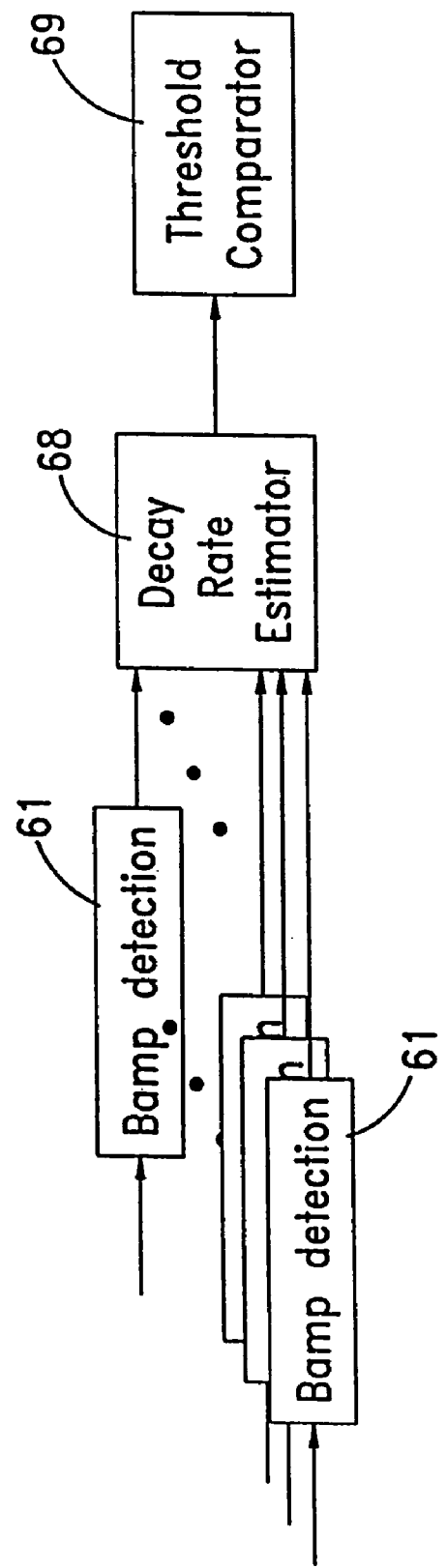

PIXEL BASED MACHINE FOR PATTERNED WAFERS

This is a Continuation Application of prior application Ser. No. 10/281,125, filed Oct. 28, 2002 (now abandoned), which is a Divisional Application of prior application Ser. No. 10/003,347, filed Dec. 6, 2001 (now U.S. Pat. No. 7,016,526), which is a Divisional Application of application Ser. No. 09/110,870 filed Jul. 7, 1998 (now U.S. Pat. No. 6,366,690); the disclosure of which is incorporated herein by reference.

FIELD OF THE INVENTION

The invention relates to the inspection of surfaces, particularly the surfaces of semiconductor wafers, intended for the detection of possible defects, particularly due to the presence of particles. More particularly the invention relates to the control of semiconductor manufacturing processes, particularly Quality Control, Process Monitoring and Control and Catastrophe Detection. The invention further comprises method and apparatus for the inline control of wafer production and the immediate recognition of any fault or irregularities in the production line.

BACKGROUND OF THE INVENTION

The detection of defects and/or of the presence of foreign substances on semiconductor wafers has received considerable attention in the art. Defects can be caused by an imperfect production of the desired pattern. Further, particles of various kinds may adhere to a wafer surface for a number of reasons.

The inspection process can be carried out on bare wafers, viz. wafers that have not yet been patterned, or on patterned wafers. This invention relates primarily to the inspection of patterned wafers.

Prior art devices are used in order to detect defects and particles of the type described above in patterned wafers. Examples of prior art apparatus comprise devices based on the direct comparison of different dies. Such apparatus, which will be further referred to below with respect to specific references, presents the following drawbacks: 1) it is relatively very expensive, as it requires high mechanical precision; 2) it has low throughput; 3) it has a large footprint; 4) it needs an expert operator; 5) it is not suitable for inline inspection (i.e., it operates on wafers which have been previously removed from the fabrication line), and therefore is unsuitable for purposes of process control and monitoring, of the kind addressed by the present invention; 6) prior art devices are non-isotropic devices, i.e. they require a very precise alignment of the article being inspected. These facts impose constructive and operative constraints on the apparatus and on the inspection method.

U.S. Pat. No. 4,731,855, to Kyo Suda et al, includes in its Background of the Invention a list of various methods for performing semiconductor wafer inspections, and said list is incorporated herein by reference. One of said methods involves scanning the wafer surface with a laser beam and analyzing the number and direction of diffraction lights, produced by the pattern edges, by means of a plurality of light detection cells arranged cylindrically.

U.S. Pat. No. 4,345,312, to Toshikazu Yasuye et al, discloses a pattern inspecting method which comprises picking up an image from an article having a preset pattern whereby to extract the data of the pattern to be inspected, converting said data into a bit matrix of binary values, and comparing said matrix with a reference matrix representing an ideal pattern, to disclose any discrepancy between the pattern of the article and the ideal one.

U.S. Pat. No. 4,342,515, to Masakuni Akiba et al, discloses an inspection apparatus for determining the presence of foreign matters on the surface of a wafer, which apparatus includes a beam generator portion which projects a collimated beam towards the object to inspect it from a side thereof, and a mechanism which senses light reflected from the surface of the object, through a polarizer plate. Such methods, however, are obsolete inasmuch as they cannot be used with today's wafers having a design rule of 0.5 µm or less.

The same principle is used in several prior art methods and apparatus. Thus, in U.S. Pat. No. 4,423,331, to Mitsuyoshi Koizumi et al, the light reflected from the wafer surface is directed to a photoelectric tube and defects are detected by the irregularities of the voltage current outputted by the tube.

U.S. Pat. No. 4,669,875, to Masataka Shiba et al, makes reference to the aforesaid U.S. Pat. No. 4,342,515, and proposes a method and apparatus based on the same principle, in which a polarized laser beam irradiates the substrate from directions inclined with respect to the perpendicular to its surface and linearly scans said surface; and light reflected from foreign particles is detected by a polarized light analyzer sand a photoelectric conversion device.

The aforesaid U.S. Pat. No. 4,731,855 discloses a method of detecting defects, e.g. foreign particles, in which the diffraction light reflected from a wafer surface is analyzed by distinguishing between normal and abnormal directions. An ideal pattern formed on a wafer reflects diffraction lights in determined directions, at certain angles, which are considered normal directions. On the other hand, foreign particles reflect the light in other, abnormal directions. Reflection of light in abnormal directions indicates a departure of the pattern formed on the wafer from the real pattern, and therefore possible defects. In the invention of this reference, the abnormal direction signals are so applied as to determine whether they represent a true defect or a practically acceptable defect. Again, this method is obsolete due to the design rule of less than 1 µm.

U.S. Pat. No. 4,814,596, to Mitsuyoshi Koizumi et al, applies the said principle of analyzing polarized reflected light to identify defects. It cites the aforesaid U.S. Pat. No. 4,342,515 as well as Japanese Patent Applications Publication Nos. 54-101390, 55-94145 and 56-30630. In the apparatus of this reference, an S-polarized beam is arranged to illuminate the pattern present on the wafer. Since the irregularities in the surface of the pattern are sufficiently small, the S-polarized light is preserved in the reflected light. An analyzer is used to cut the S-polarized light in the path of the reflected light, so that, if the reflected light includes a P-polarized light, this latter is detected by a photoelectric conversion element, indicating the presence of particles on the wafer.

U.S. Pat. No. 4,628,531, to Keiichi Okamoto et al, discloses a pattern checking apparatus, which reveals by a primary selection the presence of defects that may be tolerable or not, defined as "candidate defects". The wafers having such defects are passed to a secondary selection, which distinguishes between those that are not defects in a practical sense and are acceptable, and those that are not acceptable. False alarms, viz. the detection in the primary selection of apparent defects, which are revealed in the secondary selection not to be real defects, are said to be caused, in prior art methods based on the comparison of patterns, by an imperfect registration of the patterns to be compared.

Another method of the prior art relates to inspection apparatus employing a planar array of individually addressable light valves for use as a spatial filter in an imaged Fourier plane of a diffraction pattern, with valves having a stripe geometry corresponding to positions of members of the diffraction pattern, blocking light from those members. The remaining valve stripes, i.e. those not blocking light from diffraction order members, are open for transmission of light. Light directed onto the surface, such as a semiconductor wafer, forms elongated curved diffraction orders from repetitive patterns of circuit features. The curved diffraction orders are transformed to linear orders by a Fourier transform lens. Various patterns of stripes can be recorded and compared. Related discussion can be found in U.S. Pat. Nos. 4,000,949 and 4,516,833.

U.S. Pat. No. 5,699,447 discloses and claims an apparatus which comprises first examining means for examining in a first phase the complete surface of the wafer with an optical beam of small diameter and for outputting information, indicating inspected locations on the article's surface having a high probability of a defect, storage means for storing the output of the first examining means, and second examining means for examining in a second phase and with a relatively high spatial resolution only the locations having a high probability of a defect and for outputting information indicating the presence or absence of a defect in said locations. The first examination phase is effected by making a comparison between the pattern of the inspected wafer and another pattern, serving as a reference pattern; and the second examination phase is carried out by a similar comparison to identify the locations in which the comparison shows such differences as to indicate the presence of a defect.

The methods and apparatus of the prior art have several drawbacks, partly discussed in the cited references, such as errors due to faulty registration and other causes, false alarms consisting in the detection of defects that are only apparent, and so on. All of them, further, have the common drawback of requiring complex apparatus, with high mechanical precision, and requiring long operation times and having therefore a low throughput.

It is therefore a purpose of this invention to eliminate the drawbacks of the prior art method and apparatus for the inspection, of patterned semiconductor wafers, and particularly for determining the presence of particles of foreign substances.

It is another purpose of this invention to provide such a method and apparatus that operate at a much higher speed than prior art apparatus and with a much higher throughput.

It is a further purpose of this invention to detect the defects or suspected defects of surfaces, particularly of patterned, semiconductor wafers, by a system that does not require comparison of patterns.

It is a still further purpose of this invention to detect said defects or suspected defects by an inspection or testing of the pixels of the surface.

It is a still further purpose of this invention to detect said defects or suspected defects by an analysis of the optical response of the pixels of the surface to a scanning beam.

It is a still further purpose of this invention to provide a wafer control method that is not based on a comparison of patterns, but is a pixel-based inspection.

It is a still further purpose of this invention to provide a wafer control method and apparatus that are completely automatic and eliminate almost all possibility of human error.

It is a still further purpose of this invention to provide such a method and apparatus which are highly flexible or, in other words, that can be operated in such a way as to achieve the precision that is required in any particular processing situation.

It is a still further purpose of this invention to provide a method and apparatus for controlling the semiconductor wafers inline and immediately recognizing any failures or irregularities in the production process and apparatus.

It is a still further purpose of this invention to provide a method and apparatus that permit to localize on the wafer surface the position of any suspected defects.

It is a still further purpose of this invention to provide a method and apparatus for a primary control of semiconductor wafers that facilitates carrying out a subsequent operation called herein a "vector die-to-die comparison".

By the expression "vector die-to-die comparison" (abbreviated as VDDC) is meant, in this specification and claims, an operation the purpose of which is to determine which of the suspected defects represent valid pattern data and which represent real defects. The preferred embodiment described herein requires firstly transforming the polar coordinates of the wafer inspecting apparatus—hereinafter "the machine coordinate system"—to the Cartesian coordinates of a system hereinafter defined—"the die coordinate system of the wafer"—Then, deriving from the coordinates that define the suspect pixels' location in the machine coordinate system the coordinates that define said location in the die coordinate system. Finally, the VDDC is an operation for discriminating, between suspect data that are actually produced by the wafer pattern and suspect data that are produced by real contamination by particles—all as will be fully explained hereinafter.

It is a still further purpose of this invention to provide a method and apparatus for the analysis of surfaces, even if they are not surfaces of patterned semiconductor wafers.

It is a still further purpose of this invention to provide an optical head which comprises, in a structural unit, all the optical elements required for irradiating the pixels of the surface with the beam used for scanning and collecting their optical response in the particular manner of this invention, as hereinafter described.

It is a still further purpose of this invention to provide an apparatus which effects the control of the pixels by a combination of such an optical head and means for displacing the surface relative to it.

Other purposes and advantages of the invention will appear as the description proceeds.

SUMMARY OF THE INVENTION

The invention, both as to method and apparatus, is based on the principle of inspecting all or part of the individual pixels of the patterned wafers under control, without comparing patterns or needing specific information about the patterns. In other words, the invention is based on the principle of detecting suspected pixels, viz. pixels that show signs of having a defect, particularly the presence of foreign particles, without reference to the pattern to which the pixel belongs or to the position of the pixel on the wafer and without comparison between patterns. This inventive inspection method is termed herein "design rule check". Although reference will be made herein to patterned semiconductor wafers, the analysis of which is the primary purpose of the invention, it will be apparent that the invention can be applied in general to the analysis of different surfaces, particularly of any surfaces not patterned or having patterns the dimensions of which are similar to those of wafer patterns, e.g. in the order of microns or fractions of microns.

The method and apparatus of the invention can be used "inline", viz. is suitable to be integrated with the production process tool, using the same wafer handling and interface system, and can operate as an integrated particle monitor to provide a constant check of the wafers produced, and in this way will detect any irregularities or defects that may arise in the production line. Sometimes unforeseen phenomena may occur in the production line that are so far-reaching as to render its further operation impossible or useless. It is important to detect such phenomena, which may be termed "catastrophic", as soon as possible, and this invention permits to do so. These inline checks are rendered possible for the first time in the art by the high speed of the pixel-based inspection method and the moderate cost and footprint of the apparatus.

According to an aspect of the invention, the same comprises a method for the determination of defects, particularly the presence of foreign particles, in patterned, semiconductor wafers, which comprises successively scanning the individual pixels, defining the signature of each pixel, and determining whether said signature has the characteristics of a signature of a faultless or of a defective, or suspected to be defective, pixel.

In some embodiments of the invention, the determination of the characteristics of the pixel signatures is preceded by preliminary steps of evaluation of the characteristics of the individual signals that make up the signature, which permit to conclude that certain signatures cannot belong to defective pixels, and therefore require no further processing, whereby to reduce the amount of data that must be processed. Therefore the method of the invention may comprise defining the signature of each pixel, evaluating each signal of each signature, and, based on said evaluation, excluding a number of signatures from further processing. Preferably, the pixels are optically scanned by means of an illuminating beam and their signature is defined by their optical reaction to the illuminating light. In this case, the various embodiments of the method of the invention are characterized by the following features:

I— The type of light being used;
II—The physical and geometric parameters of the illumination;
III—The property and/or parameters by which the optical reaction of the pixels, and therefore their signature, is characterized;
IV—The physical and geometric parameters of the detection of said optical reaction.

I—The Type of Light Being Used

According to the invention, one can use laser beams or light produced by other sources, such as flash lamps, fluorescence lamps, mercury lamps, etc. Laser beams can be produced e.g. by diode lasers and have any wavelength, e.g. 400 to 1300 nm. The choice of the appropriate wavelength can be carried out by skilled persons in any case, so as to produce optimization for a given material or pattern. Relatively long wavelength (e.g. 600-810 nm) are generally preferred because of the high energy fluence achievable. Short wavelengths can be preferred for detecting small particles and for finer design rules. Laser beams can also be produced by non-diode generators, of any wavelength from IR to deep UV. The illuminating radiation may be narrow band or wide band (important for spectral analysis). It can be coherent or non-coherent, polarized or non-polarized. As to fluence, it can be CW, pulsed or quasi-CW. One or a plurality of light beams can be used.

II—The Physical and Geometric Parameters of the Illumination

1. The number of the illumination sources can be changed.
2. The geometric placement of the illumination sources can be changed.
3. The size and form of the light source and of the illuminated spot can be changed.
4. The way in which the illumination light is delivered can be changed.

Important changes can arise from changing the size of the illuminated spot with respect to a given pattern. A spot of 5 square microns will provide a completely different set of signatures than a spot of 75 square microns, and different discrimination capability. Some useful light source forms are a point source, a ring source, a large aperture source, and a line source. It may sometimes be beneficial to illuminate through the wafer (or through another article, when such is being inspected, such as a reticle or some other transparent article) with a relatively large wavelength (more than 1 micron). Thus, one could illuminate from beneath the wafer and collect the received radiation from above.

The illumination light can be delivered by optical trains, fiber optics, or other directing elements.

III—The Property and/or Parameters by Which the Pixel Signatures are Characterized 1. In this system, the energy of the scattered light is the main property that is being measured.
2. Another property is the height of the surface. This is measured by the height measurement system.
3. Other properties can also be used successfully for creation of a signature. These are:
3.1. The polarization of the received radiation, in P and S planes. This is important, since there are many geometric locations at which the pattern on the wafer induces a well determined polarization, so that a correctly aligned polarizer would sense only particles.
3.2. The phase of the received radiation.
3.3. The wavelength of the received radiation, which can be tested in various ways, e.g. by testing for fluorescence or by testing the spectral response of a pixel.

With reference to the polarization of the received radiation, it has been shown (see J. M. Elson, Multilayer coated optics: Guided wave coupling and scattering by means of interface random roughness, J. Opt. Soc. Am. A12, pp. 729-742 (1995)), that the polarization direction field around a patterned wafer surface, when illuminated with polarized light, exhibits a phenomenon whereby at certain collection angles the polarization field is well defined. Thus, with a properly aligned polarizer, the light scattered from the pattern will contribute almost zero energy at said angles. On the other hand, if there is a particle in the illuminated spot, the light scattered from it is depolarized, and will contribute significant energy at said angles, whereby the particle will be clearly detected. It is not necessary to fix precisely the location and polarization direction of the detectors that will permit to detect a particle in this way: it suffices to provide a sufficiently high number of detectors, each with a polarizing sheet in front. The plurality of detectors ensures that some of them will get a response that will indicate the presence of a particle. When using polarized light, therefore, the method and apparatus of the invention need not be modified as to the way of delivering the illuminating light and detecting the light scattered from the wafer pixels, but a polarizer should be placed in front of each detector, no other change being required in the apparatus, and the signal processing algorithms should be modified to take into account the fact that the detectors which generally capture low levels are those placed at the aforesaid angles in which the polarization field is well defined, so that if the light collected by those detectors has significant energy, the algorithm should signal the presence of a particle.

IV—The Physical and Geometric Parameters of the Detection of the Optical Reaction of the Pixels The optical reaction, and therefore the signature of the pixels is defined by the light scattered by the pixels. The way in which it is detected can vary widely. It is detected in a plurality of directions, which will be called, for descriptive purposes, "fixed directions". Each direction is defined by a line from the pixel to a point of light collection. Therefore, the geometry of the scattered light detection is defined by the disposition of the points of light collection. Said points may be disposed e.g. in azimuthal symmetry on horizontal concentric circles ("horizontal" meaning herein parallel to the wafer surface), or in elevational symmetry on vertical or slanted semi-circles, or in a flat grid parallel to the wafer surface, or in a semi-spherical or other vault-like arrangement above the wafer.

In a preferred form of the invention, said signature is defined by an array of signals, each of which measures the intensity of the light scattered by the pixel in a direction, and will be called herein "signature component". The number of directions in which said intensity is measured, and therefore the number of signature components should be sufficiently high for the signatures to characterize the corresponding pixels, as hereinafter better explained. The said signals are sampled at a given frequency "f", which will be called "the sampling frequency". The period of time between successive samplings, $t=1/f$, will be called "the sampling period". The sampling frequency used in carrying out the invention is preferably very high, in the order of millions of Herz, e.g. 11 Mhz. Each sample generates an array of digital signals, which defines the signature of the pixel that was illuminated by the beam at the moment the sample was taken.

The term "scanning beam" is to be construed herein as meaning a beam that has a relative motion with respect to the wafer and successively impinges on different points of the wafer. The invention comprises relative motions of any kinematic nature and produced by any mechanical means, as long as they cause the spot of the beam to move over the wafer surface. By "spot of the beam" (also called "the beam footprint") is meant the area of the wafer illuminated by the beam at any moment, or in other words, the intersection of the beam with the surface of the wafer. In view of the relationship between the wavelength of the scanning beam and the dimensions of the elements of the wafer pattern and of the foreign particles, the light scattered by the wafer is diffracted.

The term "pixel", as used in this specification and claims, means the area covered by the spot of the beam at the moment a sampling is carried out, viz. the moment at which the digital signals, representing the intensity of the light scattered by the wafer in the fixed directions, are determined. Ideally, each pixel should border on the pixels adjacent to it, but this is not necessary for successfully carrying out the invention. In practice, depending on the character and speed of the relative motion of the scanning beam with respect to the wafer, on the area of spot size, and on the sampling frequency, adjacent pixels may overlap, so that each point of the wafer is examined more than once, or, on the contrary, the adjacent pixels may be spaced from one another, so that not all the points of the wafer will be examined. One or the other relationship between pixels may be chosen, and the relative motion of the scanning beam with respect to the wafer may be determined as desired, taking into account such parameter as the resulting amount of data and the speed of the operation.

In order to determine whether a signature has the characteristics of a signature of a faultless or of a defective pixel, any criterion that is adapted to the specific conditions in which invention is carried out, and provides the desired type and degree of selection, can be adopted. The criterion may comprise a comparison between the controlled signature and a master signature, or the definition of ranges of acceptable parameters in which the parameters of the controlled signature must be included, or the position of the controlled signature in a statistics of signatures, and so on. A broadly suitable and simple method will be described hereinafter by way of example.

According to another aspect of the invention, at least one source of an irradiating beam, preferably a laser diode, is provided and is preferably motionless, the controlled wafer is preferably rotated, more preferably about its center, and is translated (viz. displaced parallel to itself along a straight or curved line), preferably by displacing its center in a line that lies in a plane perpendicular to its axis of rotation, so as to move the spot of the beam over the surface of the wafer, and the light scattered by the wafer is collected in a plurality of directions. These directions, in which the scattered light is collected, will be called hereinafter "fixed directions". The rotary motion of the wafer has considerable advantages, in particular it is easy to effect by mechanical means of conventional precision and permits to achieve very high process velocities and therefore a very high throughput, while having a small footprint. Although a rotational and a translational motion of the wafer, the scanning beam being motionless, have been mentioned hereinbefore as preferable, it is the relative motion of the beam with respect to the wafer that is the determining factor, and any manner of obtaining it is equally within the scope of the invention. Preferably, in each fixed direction the collected light is transduced to an electric signal and this latter is converted to a digital signal—a pixel component—by sampling.

In a variant of the above aspect of the invention, a single scanning beam is provided and the wafer is so moved that said beam scans the entire surface of the wafer. A plurality of lasers, the spot sizes of which substantially overlap, are considered herein as producing a single scanning beam.

In another variant, the surface of the wafer is partitioned into a number of zones, a number of scanning beams (preferably equal to said number of zones) is provided, each scanning beam being associated with one of said zones, the inspected wafer is so moved that each beam scans the wafer zone associated with it, and the light produced by the scattering of each beam by the wafer surface is collected in a plurality of fixed directions associated with said beam. Typically and preferably, said zones of the wafer, except the central one, which is circular, are annular, concentric rings having similar radial dimensions, and the wafer is rotated and is shifted approximately radially by an amount equal to said radial dimension of the rings. This variant of the invention shortens the processing times, requires smaller motions of the apparatus elements and permits to define smaller pixels.

In a further preferred form, the process of the invention comprises the following steps:

1—irradiating each wafer with one laser beam or with a plurality of laser beams;

2—causing a relative motion of each wafer with respect to said beam, if one laser beam is used, to cause said beam to scan the wafer, and if a plurality of laser beams is provided, to cause each beam to scan a zone of the wafer associated with it;

3—sensing the light scattered by the wafer in a plurality of fixed directions, if a single beam is provided, or in a number of such pluralities associated each with a beam, if more than one beam is provided;

4—converting said scattered light, in each fixed direction, to an electric signal;

5—sampling said electric signal at a predetermined sampling frequency, whereby to determine, at each sampling, an array of values, one value in each fixed direction, associated with a pixel of the wafer;

6—considering each said array of significant values as constituting a pixel signature;

7—defining the conditions which must be satisfied by all the pixel signatures of a faultless wafer;

8—determining whether the pixel signatures of each wafer meet the said conditions; and 9—classifying the pixels which meet the said conditions, as acceptable pixels and the remaining pixels as "suspect".

In an embodiment of the invention, a group of beams may be used to scan a wafer by focusing them so that all have the same spot on the wafer surface. In this case, the scattered light produced by all the beams will be collected in the same fixed directions.

Concurrently with the identification of the suspect pixels, their location on the wafer is recorded to permit successive vector die-to-die comparison. At each moment of the process, the position of the pixels under examination is identified in the machine coordinate system. In that system, the position of each pixel is defined by the angle by which the wafer support has rotated and by the distance of the pixel from the wafer center, or, as may be said, its radial position, which depends on the displacement which the wafer center has undergone with respect to the laser beam. Said angular and radial positions constitute the polar coordinates of the pixels. The position of the pixel on the wafer, on the other hand, is defined in the die coordinate system, in which a point is identified by the index of the die it is in and the coordinates of the point inside the die, with the axes parallel to the principal directions of the die and the distances measured in microns. The way in which the die coordinates of a point are calculated will be described hereinafter.

In a preferred form of the invention, the signatures of the pixels are transmitted, together with their coordinates, to a hardware component of the apparatus. By "hardware component" is meant herein an electronic device having a specific task or a number of specific tasks which can be selected as desired in each case. In general, the hardware component is a specially designed digital electronic device, the task of which is to analyze the signals and make the preliminary selection between signals that represent a valid pattern on the wafer and those that are suspected to arise from a contaminated spot. The signatures of the suspect pixels and their coordinates are transmitted further to a software component, which completes the die-to-die comparison. It will be understood that, since the suspect pixels are only a small fraction of all the wafer's pixels, the information thus outputted by the hardware component is a small fraction of the information received by it.

An embodiment of the invention therefore comprises determining the position of the apparently defective pixels in the suspect wafers. Another embodiment of the invention comprises measuring the height of the pixels. Each type of wafer has a pattern having a given depth. Large foreign particles often have a height, viz. a dimension perpendicular to the wafer surface, in excess of said depth of the wafer pattern, and therefore protrude from said pattern and their presence can be detected by a height measurement.

The invention further comprises an apparatus for the determination of defects, particularly the presence of foreign particles, in patterned, semiconductor wafers, which comprises:

a) a turn table for supporting a wafer and rotating it;

b) a light source and optics for generating at least one light beam and directing it onto the wafer;

c) means for shifting the spot of said beam relative to the wafer center, preferably by shifting the axis of rotation of the wafer;

d) collection optics for collecting the light scattered by the wafer in a number of fixed directions;

e) photoelectric sensors for generating electric analog signals representing said scattered light;

e) A/D converter for sampling said analog signals at a predetermined frequency and converting them to successions of digital components defining pixel signatures;

f) means for determining the coordinates of each pixel;

g) a hardware filter for receiving the pixel signatures and their coordinates and identifying the signatures that are not signatures of faultless pixels, viz. that are signatures of suspect pixels; and h) a software algorithm for receiving from the filter the signatures of suspect pixels, together with the corresponding pixel coordinates, and carrying out a vector die-to-die comparison.

In a preferred embodiment of the apparatus according to the invention, the light beam is a laser beam. In a more preferred embodiment, the means for generating a laser beam and the means for collecting the laser light scattered by the wafer in a number of fixed directions are associated, in the appropriate geometrical relationship, in a single structural unit, herein called "optical head". An optical head generally comprises a single laser generator, but if it comprises more than one, the generators are so focused as to produce a single illumination spot.

In said embodiment, therefore, the apparatus comprises:

a) a turn table for supporting a wafer and rotating the same about an axis of rotation that coincides with the geometric axis of the wafer;

b) means for translationally shifting the axis of rotation of the wafer;

c) at least one optical head;

d) photoelectric means for transducing the optical signals generated in said optical head to electric analog signals;

e) A/D converter for sampling said electric analog signals at a predetermined frequency and converting them to successions of digital components defining pixel signatures;

g) a hardware filter for receiving the pixel signatures and their coordinates and identifying the signatures that are not signatures of faultless pixels, viz. that are signatures of suspect pixels; and h) a software algorithm for receiving from the filter the signatures of suspect pixels, together with the corresponding pixel coordinates, and carrying out a vector die-to-die comparison.

The optical head is, in itself, an object of the invention.

In an aspect of the invention, the apparatus comprises, in combination with mechanical means for supporting and rotating a wafer, optical means for substantially isotropically collecting the light scattered by the wafer, and hardware means for taking into account any angular displacement of the principal directions of the wafer dies with respect to the wafer support plate. By "substantially isotropically collecting the scattered light" is meant collecting it at capture angles that are so many and densely distributed that an angular displacement of the optical collecting means will not significantly change the optical signals so collected. In other words, the optical collecting means will behave approximately as if they were constituted by rings, set in planes perpendicular to the axis of the wafer rotation, uniformly sensing the scattered light at every point thereof. The means for taking into account any angular displacement of the principal directions of the dies, with respect to the wafer support plate, comprises means for transforming the optical signals actually received to the values they would have if all the wafers were mounted on their support plate with their principal directions set in an invariable, predetermined orientation.

The signature of any given pixel depends on certain operating parameters, which must be specified and remain constant in any reduction to practice of the invention. The parameters comprise: a) the characteristics of the irradiating light, such as the type of light sources, the number of such sources, the direction of the irradiating beam or beams, their wavelength, their energy fluence, the area of their spot size, etc.; b) the fixed directions, viz. their number and their orientation, both as azimuth and as elevation with respect to the substrate surface; c) the solid angle within which reflected light is sensed by each sensor. Other parameters, referring to the mechanics of the invention, will become apparent later. If any of said parameters is changed, the pixel signatures will change correspondingly. Therefore, said parameters must remain the same in any operation carried out according to or for the purpose of this invention. Generally, the larger the number of fixed directions, the better the resolution of the scattered light and the completeness of the pixel signatures. Structural considerations, on the other hand, prevent using an excessive number of them. It has been found that a satisfactory compromise between said contrasting factors is to use 16 or 32 fixed directions and corresponding scattered light collectors. For simplicity of illustration, in the following description, it will be assumed that there are two superimposed rings of fixed directions, each of which comprises 16 fixed directions. In each ring, the fixed directions are uniformly spaced in azimuth and have the same elevation angle. The two rings have different elevation angles. By "elevation angle" is meant herein the angle which the direction makes with the plane of the wafer. The plane of a wafer is defined as the plane of its upper surface. The azimuthal and elevational angles are determined so that all fixed directions intersect the plane of the wafer at the same point. The aforesaid fixed direction configuration may also be described by saying that said directions lie on two conical surfaces having as their axis the axis of the wafer and a common vertex, and that they are evenly spaced on each conical surface.

The scattered light is preferably collected by at least one optical fiber bundle for each fixed direction, and transmitted to photoelectric detectors, in each of which a continuous signal is generated. The terminals of each bundle, which lie on the fixed directions, preferably abut on one another, so that each ring of optical fiber terminals, lying on one of said conical surfaces, is continuous. It can be said that the optical fiber bundles are preferably "interlaced". The photodetectors, which are conventional apparatus (an example of which is OSD50, manufactured by Centronics), produce continuous electric signals. The sampling of the continuous electric signal produced by each photoelectric detector, can be carried out by apparatus known in the art and available on the market (e.g. AD9059RS, manufactured by Analog Modules) at frequencies of millions of Hz, so that the number of pixels for which a signature is obtained is in the order of millions per second, e.g. 11 Mpix/sec.

The scanning beam generally has an oblong spot size, e.g. having a radial dimension (viz. a dimension parallel or approximately parallel to the wafer radius) between 5 and 15 microns and a tangential dimension (viz. a dimension perpendicular to the radial one) between 3 and 5 microns.

BRIEF DESCRIPTION OF THE DRAWINGS

In the drawings:

FIG. 8 is a block diagram generally illustrating the phases of the scattered light processing according to an embodiment of the invention;

FIG. 9 is a block diagram generally illustrating the analog processing unit of an apparatus according to an embodiment of the invention;

FIGS. 10, 11 and 12 an embodiment of the signal processing;

DETAILED DESCRIPTION OF PREFERRED EMBODIMENTS

Figure 1:
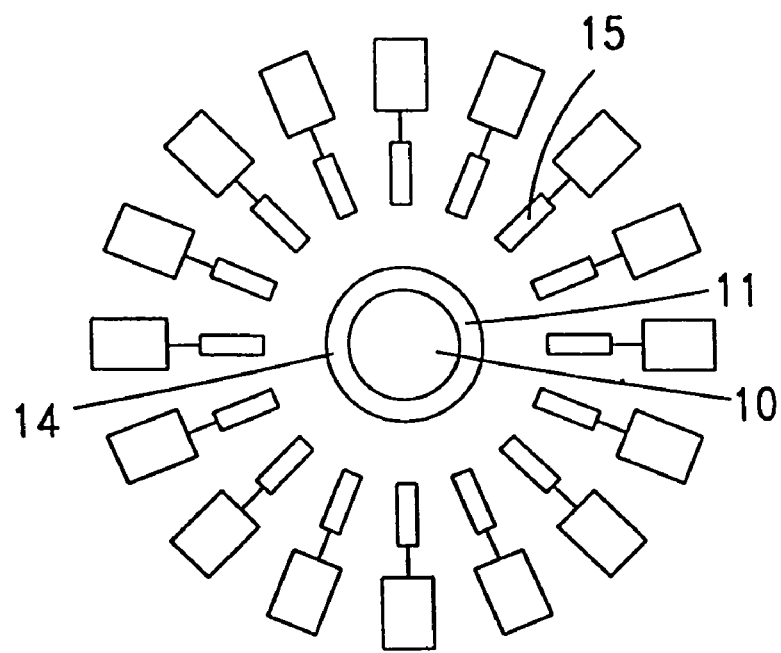
FIG. 1 is a schematic illustration, in plane view, of the general features of an apparatus according to an embodiment of the invention.
Figure 2:
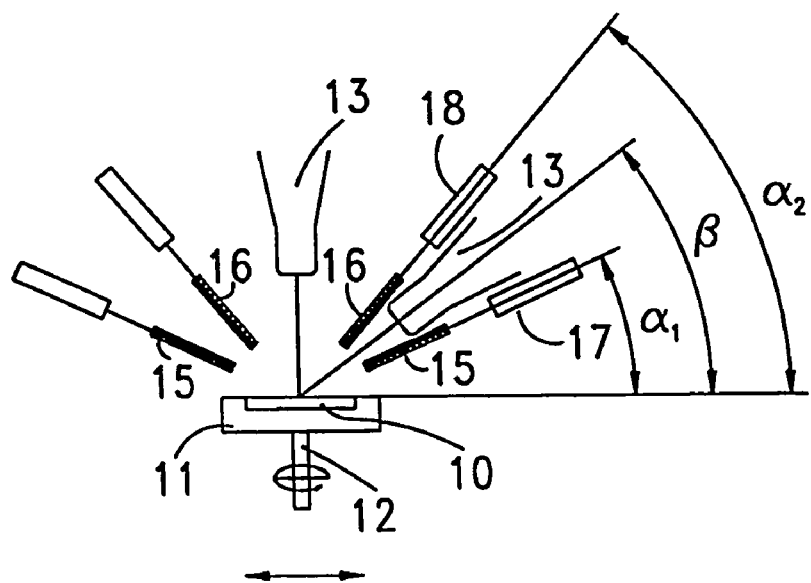
FIG. 2 is a schematic illustration, in elevational view, of the apparatus of FIG. 1.

FIGS. 1 and 2 schematically represent an apparatus according to an embodiment of the invention. Numeral 10 indicates a wafer that is being inspected. The apparatus used for the inspection comprises a stage having a wafer support. The wafer is placed on said support, which in this embodiment is a support plate 11, which is rotated about shaft 12 by mechanical means, not shown as being conventional. A laser source is shown at 13 in its central position, above the axis of shaft 12. However, more than one source could be provided and any source could be placed at an angle to the axis of shaft 12, to provide the required illumination of the wafer, depending on the type of wafer under inspection. In FIG. 2 one such additional laser source is shown, by way of illustration, oriented at an angle β from the plane of the wafer. Mechanical means, not shown as being conventional, translate the shaft 12, viz. shift it, while maintaining it parallel to itself, so that any point thereof moves in a straight or curved line that lies in a plane perpendicular to the axis of the shaft. Consequently the wafer 10 is also translated parallel to itself so that its center of the wafer is shifted in a plane perpendicular to the axis of the shaft. By "translatory motion" is meant any motion of a body in which the body does not rotate, but is displaced without rotation along any straight or curved line. The translational displacement of shaft 12 and wafer 10 is rectilinear, but it need not be: if desired, it could follow a curved path.

Additionally, the laser source or sources may not be stationary and the corresponding spot or spots on the wafer surface may move in a way similar to the motion of a needle on a phonograph disk, viz. swing along an arc of circle passing through the center of the wafer. Consequently, since the laser source 13 remains stationary, the spot of the scanning beam is displaced on the wafer from the periphery of the wafer to its center and/or vice versa, and, possibly but not necessarily, along or approximately along a radius of the wafer 10. Preferably, the wafer is rotated at a $V_r$ of 5000 rpm and displaced radially at a speed L of 0.01-0.5 cm/sec.

The light of beam 13 is scattered in the fixed directions. The fixed directions may be azimuthally or elevationally distinct. In the embodiment illustrated, they are azimuthally distinct and arranged in 2 rings of 16 each. In each ring, the said directions are symmetrically arranged about the wafer and slanted at an elevation angle $\alpha_1$ for the lower ring and $\alpha_2$ for the upper ring, from the plane of the wafer. The angle $\alpha_1$ is selected from 8 to 15 degrees, and the angle $\alpha_2$ from 15 to 30 degrees. This arrangement, however, is merely an example, and can be varied as desired, as will be better-explained later.

In each fixed direction, the scattered light is collected by an optical fiber terminal—15 in the lower ring and 16 in the upper ring. Preferably, the generator of the beam 13 and the optical fiber terminals are structurally associated in an optical head. Each optical fiber transfers the collected light to a photodetector—17 in the lower ring and 18 in the upper ring.

Each photodetector outputs an electric signal, which is transmitted to an electronic circuit, not shown in the drawing, which samples the electric signals and outputs, for each fixed direction, a digital signal corresponding to the intensity of the light collected by the corresponding optical fiber. The sampling frequency f may be, e.g., 11 MHz. The spot size of the scanning laser beam, in this example, has an approximately elliptical shape, with a longer diameter of 15 μm and a shorter diameter of 5 μm.

Figure 3:
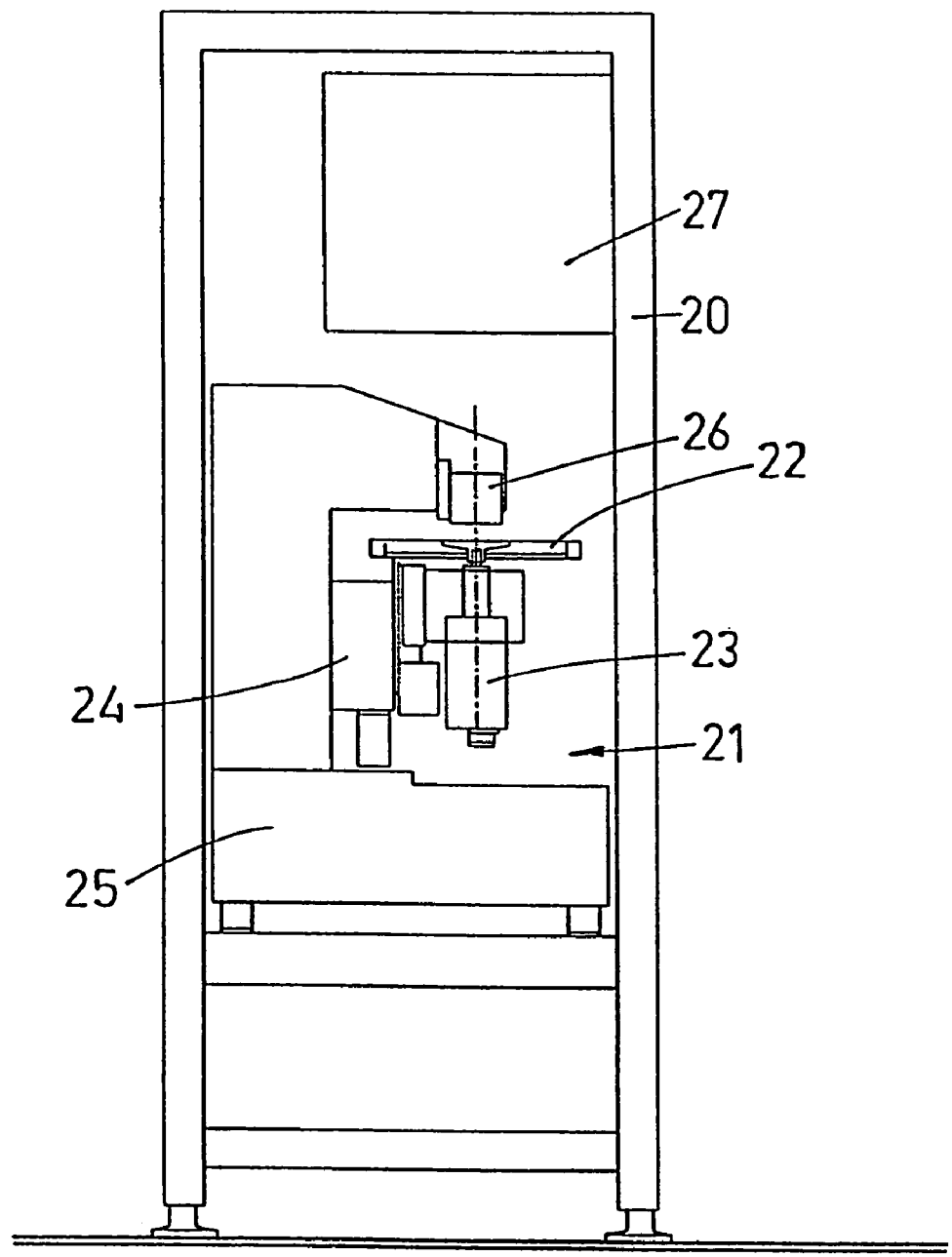
FIG. 3 is a schematic illustration, in elevational view, of an apparatus according to an embodiment of the invention.

FIG. 3 is a further schematic illustration, in elevational view, of a machine according to an embodiment of the invention. The machine comprises a frame 20, on which a mechanical assembly, generally indicated at 21, is supported. The mechanical assembly comprises a motor assembly 23, which rotates a plate 22 that supports the wafer. Numeral 24 schematically indicates means for translationally displacing said motor and plate. Numeral 25 generally indicates a scanning system, which actuates a scanning head 26, containing the laser sources, the optical fibers for collecting the scattered light, and the photoelectric detectors. Block 27 schematically indicates the electronic components of the machine, which receive the output of the photodetectors through connections (not shown) and process it as herein described.

It should be noted that, besides the aforementioned rotary and translational motions of the wafer supporting plate, which occur during the scanning of the wafers, different motions are required for carrying out the stages of loading and unloading the wafers. Additionally, an autofocusing mechanism is preferably provided for focusing the illuminating beam, and such mechanisms (too) are well known to persons skilled in the art and need not be described.

Figure 4:
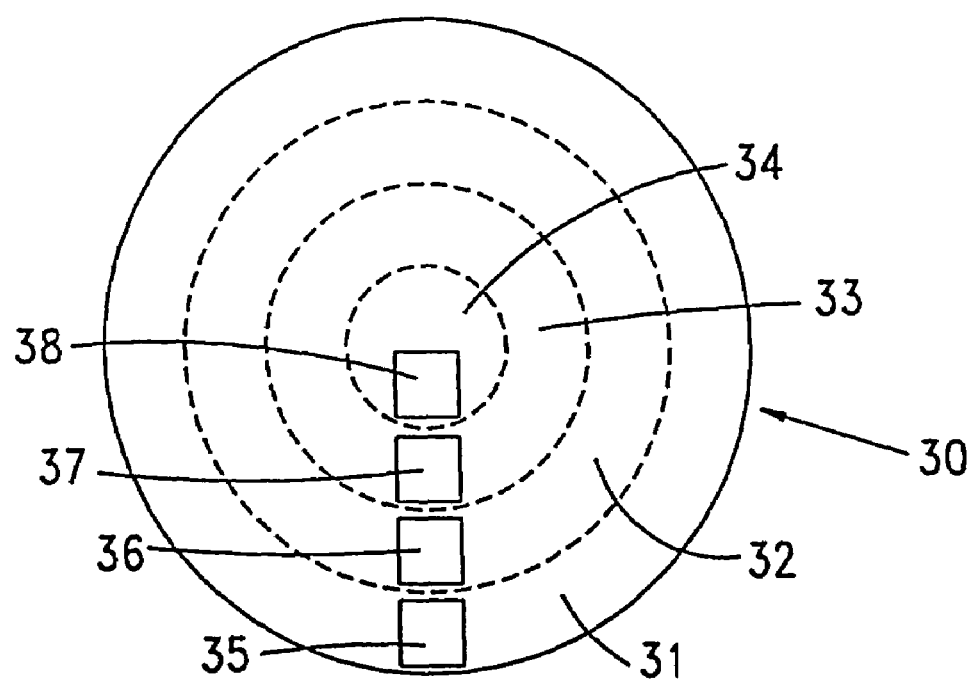
FIG. 4 is a schematic plan view of another embodiment of the invention.

FIG. 4 is a plan view schematically illustrating another embodiment of the invention, which comprises a plurality of optical heads. The wafer 30 is ideally divided into a number of zones constituted by concentric rings and a central circle. Only three ring zones—31, 32 and 33—in addition to central circular zone 34, are shown in the drawings for simplicity of illustration, but in practice there may be more. An optical head, comprising a scanning beam and an array of optical fiber sensors in the fixed directions, is provided for each zone.

Figure 5:
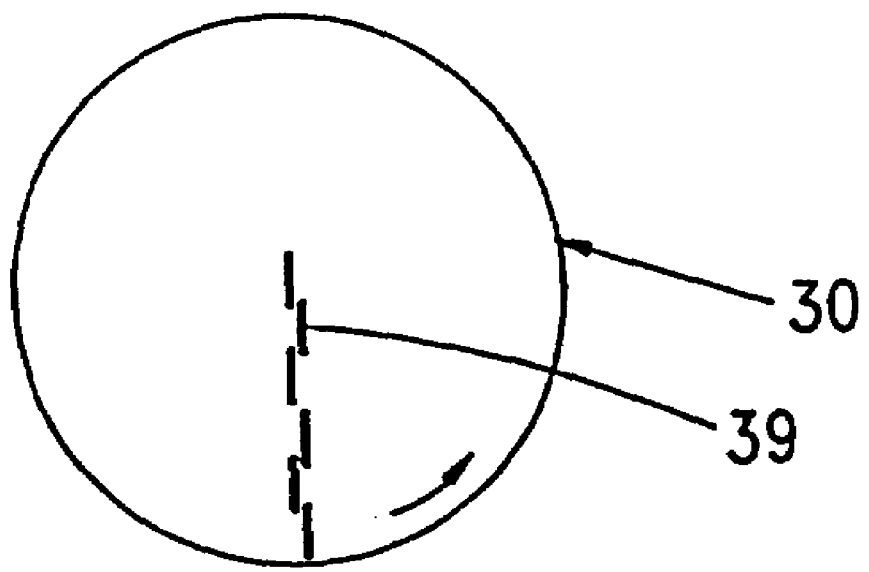
FIG. 5 is a schematic plan view of a variant of the embodiment of FIG. 4.

In each fixed direction the scattered light is collected by an optical fiber sensor. In this embodiment, the scanning beam and the optical fiber sensor of each zone are mounted on a common support, to define an optical head, hereinafter described. The four optical heads, which are identical, are indicated by numerals 35, 36, 37 and 38. In FIG. 4 the optical heads are shown as being one for each zone and successively aligned along a radius of the wafer, but this is merely a schematic illustration. The heads may not be aligned along a radius, but, for example, may be staggered and partially overlap, so that some circles drawn on the wafer surface may cross more than one head. Such an arrangement is schematically indicated in FIG. 5, wherein a plurality of heads, schematically indicated at 39, are staggered generally along a radius of a wafer 30, to cover an equal number of zones not indicated in the figure. Said arrangement particularly applies to optical heads that comprises CCD detectors, that will be described hereinafter with reference to FIG. 15.

The purpose of these embodiments is to cause a plurality of pixels to be illuminated and checked concurrently, whereby the process is accelerated and the throughput increased; and further, to limit the translational displacement of the wafer to a fraction of what it would be if a single optical head were to scan the whole wafer, simplifying the mechanics of the machine and reducing its footprint. The translational displacement, as in other embodiments of the invention, need not be radial, but may follow a differently directed straight path or a non-straight path, as may be more convenient in view of the mechanics of the apparatus. Any disposition of optical heads and/or wafer translation that will serve the purpose of a complete scanning by convenient mechanical and optical means can be adopted.

Figure 6A:
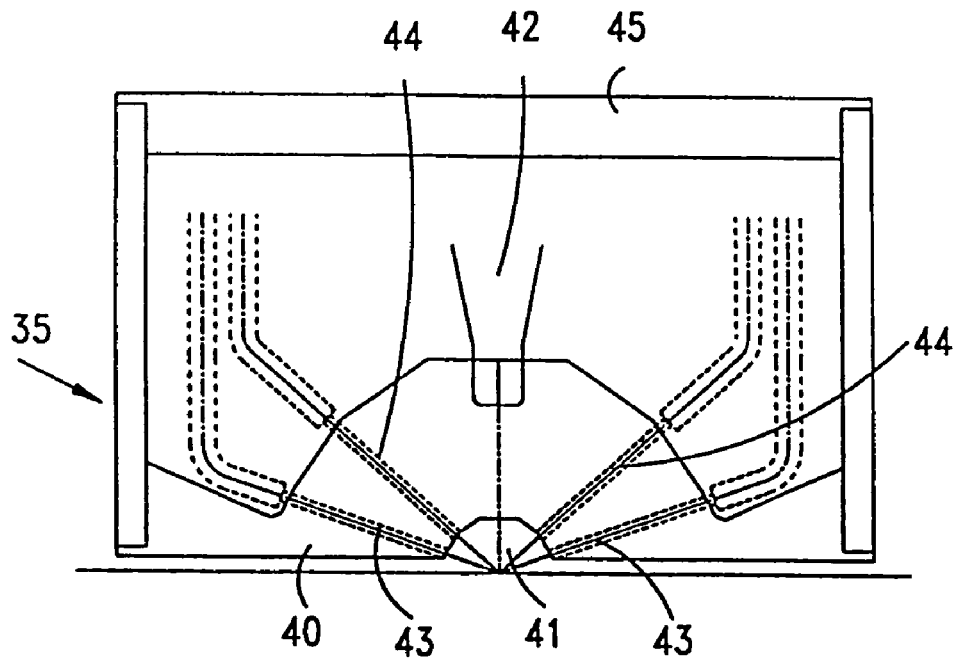
FIGS. 6a and 6b are schematic vertical cross-sections of two embodiments of optical head.
Figure 7:
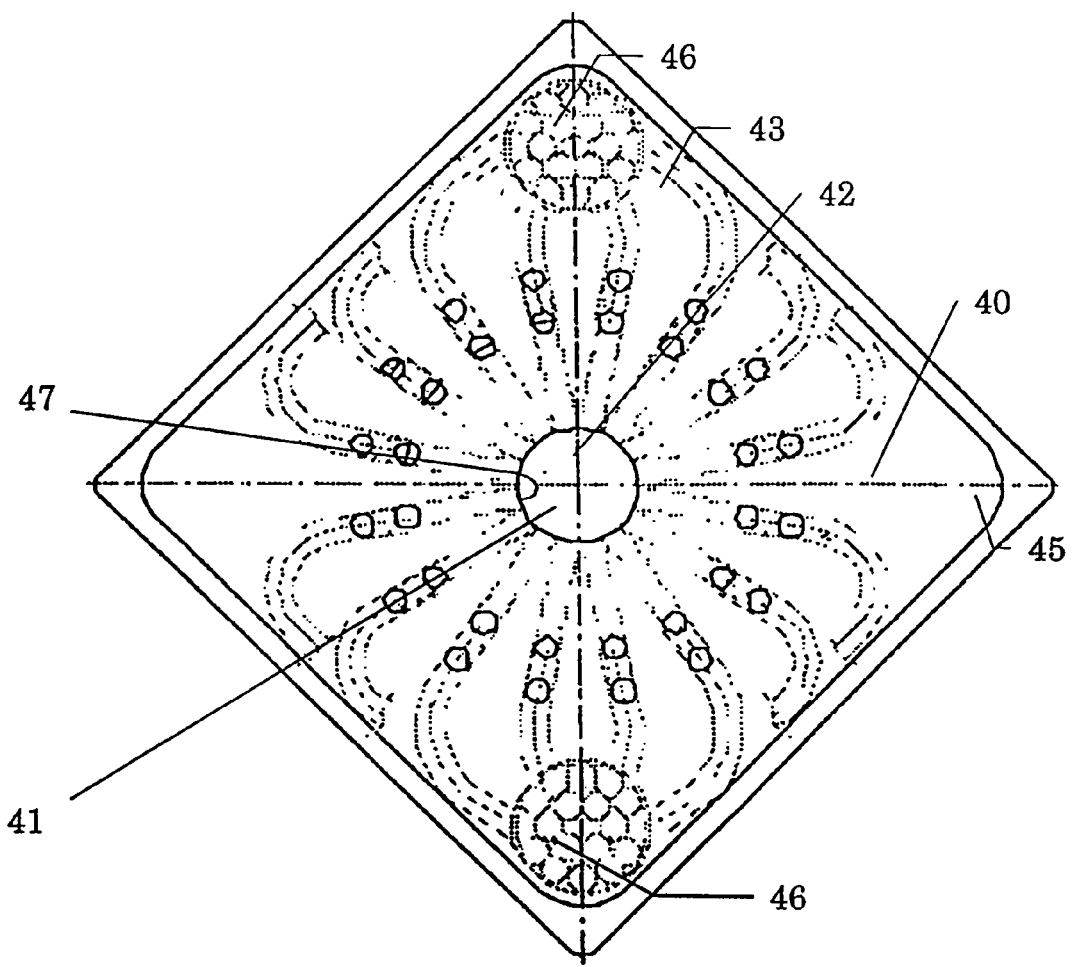
FIG. 7 is a plan view, from the bottom, of said optical head, at a greater scale.

FIG. 6a is a vertical cross-section of one of the optical heads, of which FIG. 7 is a plan view, from the bottom, at a larger scale. It is assumed to represent one of the optical heads 35 (or 39) but could represent any other optical head. It could also represent the optical head of an apparatus which includes only one such head, the wafer being displaced in such a way that the single head scans its entire surface. Head 35 comprises a base 40, which has at its bottom, a central recess or cavity 41 that is arc-shaped, e.g. approximately semi-spherical, and has a bottom, viz. its opening, that will be parallel to the plane of wafer when the head is used. Base 40 is mounted in a case 45, supported in the machine in any convenient way, not illustrated. In base 40 are mounted the laser source 42 and two circular arrays of optical fibers 43 and 44, disposed one above the other at different angles so as to converge onto the center of recess 41, where the pixel that is being examined is located. It is seen in FIG. 7 that the terminals of said optical fibers, one of which is indicated by numeral 47, which constitute the intersection of said fibers with the surface of cavity 41, are adjacent to one another, so that each array of said fibers forms a continuous circle at the surface of cavity 41. While two fibers 43 and two fibers 44 are shown in the cross-section of FIG. 6a, each array preferably comprises, in this embodiment, 16 optical fibers, which are gathered, in this embodiment, into two bundles 46 for connection to photodetectors, not shown. Further, a plurality of laser sources, e.g. placed at different angles to the wafer plane, and more than two circular arrays of optical fibers could be comprised in an optical head. No matter how many rings of fiber terminals are provided, said terminals are preferably disposed in each ring at uniform angular distances from one another and are so slanted that all of their axes pass through a common point, which is the center of the bottom of cavity 41 and will be the center of the portion of the wafer surface exposed by said cavity, when the optical head is superimposed to a wafer surface to carry out the process of the invention.

Figure 6B:
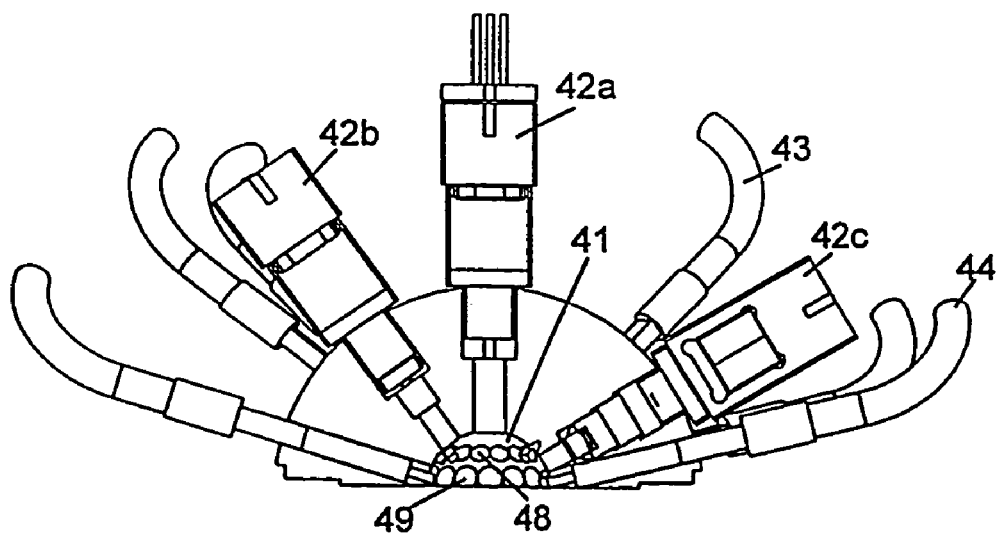

FIG. 6b schematically illustrates in vertical cross-section, at a larger scale, the optical components of another embodiment of optical head. Said head comprises three laser sources 42a, 42b and 42c, the first oriented perpendicularly to the bottom of cavity 41 and the others at different slants thereto, to provide an improved illumination. Two circular arrays of optical fibers 43 and 44 are provided in this head as well, and their terminals 48 and 49 form two circles about cavity 41. It should be appreciated that the laser source 42 can be situated remotely from the optical head 35, and that the laser beam can be transmitted to the head using, for example, other optics similar to collection optic fibers 43 and 44.

FIG. 8 is a block diagram generally illustrating the phases of the process by which the scattered light from a wafer surface is processed according to an embodiment of the invention. The process is illustrated with respect to an optical head, as hereinbefore illustrated. If the apparatus of the invention comprises a plurality of optical heads, the same operations are carried out with respect to each of them. If the optical components of the apparatus are not combined in an optical head, and no matter how they are combined, what will be said about an optical head will apply to the processing of the light scattered by the wafer surface is carried out in the stages shown in FIG. 8. It is assumed for illustrative purposes only that the optical head unit 50 includes an illumination apparatus, two rings with 16 optical fibers each, which detect the light scattered in as many directions (which constitute the fixed directions), and any supporting subsystems that it is desired to introduce, such as auto-focus mechanism, lenses, etc. The optical components operate as hereinbefore described.

The analog processor unit 51 is responsible for detecting the optical signals from the optical fibers, transducing the signals into electric pulses, amplifying said electric signals, applying a correction computation to make sure that all the detectors (32 in this example) are properly calibrated with respect to the inspected surface and with respect to each other, and finally converting each electric analog signal into a digital signal, preferably with 8 bits.

That is, each sample or pixel signature component is a digital signal constituted by a word having a sufficient number of bits to provide adequate information. E.g., the word may be composed of 8 bits, providing 256 levels of scattered light intensity. Each ring of the photodetectors will then contribute 16×8=128 bits with a frequency "f", which, in this embodiment, is assumed to be 11 Mhz.

The digital signals are transferred as output to a signal processor unit 52. The resulting pixel signature outputs must be evaluated according to a predetermined criterion. While, within the scope of this invention, many criteria and corresponding algorithms could be used, according to cases and to the choice of the expert person, a simple criterion will later be described by way of illustration.

The signal processor unit 52 is responsible for the first stage of the data reduction. It receives the input signals (32 in this example) from the analog processor unit, at the clock rate of the system (e.g. 11 MHz). It outputs only a small percentage of these data to the next stage. The signal processor unit is a custom designed electronic subunit that can handle very wide input data at a high rate. It is also capable of employing several different reduction algorithms, switching between them as the application requires. The pixels, the data of which are transmitted out of the signal processor, are henceforth termed "suspect pixels" or "suspects". The signal processor is designed to transmit a small fraction of the inspected pixels to the following unit. This data is communicated via a FIFO bank (to coordinate the communication rates), through a standard bus, such as a PCI bus, to the main CPU of the system.

The defect detection unit 53 is a software module running on the main CPU of the system. It receives suspect pixel data from the signal processor unit. Its responsibility is to separate the valid pixels from the defective ones and output the defect list as the final product of the system.

Considering now the components of the block diagram of FIG. 8 individually, the preferred structure of the Optical Head Unit 50 had been discussed hereinbefore.

The internal structure of the Analog Processor Unit 51 of this example is schematically illustrated in FIG. 9. The unit is composed of a number of identical channels, one for each optical fiber, three of which are symbolically indicated in perspective relationship. Each channel (out of the 32 of this example) comprises a detector 55 that transduces the light signal into electric current. The electric signal is then is amplified in a preset amount in a preamplifier 56. The signal is then further amplified with an amplifier 57 that has variable gain and offset. This allows the system to adapt to varying substrates, illumination angles and parameters such as wavelength, intensity, etc., and also allows calibrating the several channel signals to respond equally. This insures the isotropy of the whole optical channel, so that if the same pixel is observed from varying angles (for example, after rotation of the wafer), the same signature will be obtained from all the signals. It is also a prerequisite for all subsequent treatment of the signals. The last block of this Analog Processor Unit is an A/D converter 58 that performs analog to digital conversion preferably at 8 bits. Thus, in this example, the output of Analog Processor Unit 51 is 32 signals, each with 8 bits, at a system clock of 11 MHz.

The Signal Processor Unit 52 is a specially designed digital electronic device, the task of which is to analyze the signals and make the preliminary selection between signals that represent a valid pattern on the wafer, and those that are suspected to arise from a contaminated spot. Such suspected signals are passed on to the next analysis step. Preferably, this unit should be reconfigurable to apply various algorithms for the discrimination between valid and suspect pixels, changing the algorithm according to the demands of the application. The operation of this unit will be explained in algorithmic building blocks. The implementation of the algorithms as a hardware device is well known to electronic engineers skilled in the art of designing modern digital signal processing boards, especially of the kind that is based on FPGA (Field Programmable Gate Array) and DSP (Digital Signal Processor) technology. The details of this implementation are not part of the invention and need not be discussed herein.

While a variety of algorithms may be devised and used by skilled persons, a specific algorithm will be described by way of example, with reference to FIG. 10.

Figure 11:
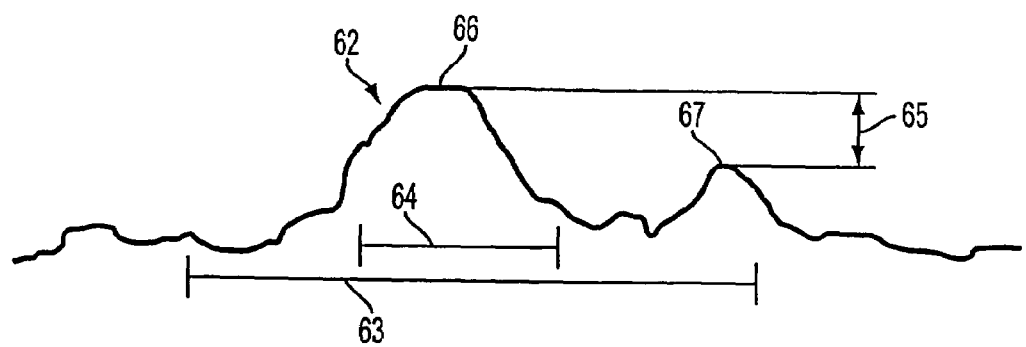

The digital signals from Analog Processor Unit 51 (32 in this example) firstly enter into a bump detector 61, each signal independently of the others. The bump 62 is graphically illustrated in FIG. 11. It is detected with the following operator, that requires three parameters: total width 63, central width 64 and a ratio threshold 65 between the brightness peak 66 of the pixel currently under control and the highest brightness peak 67 in the filter's domain that is outside a central patch. By "width" is meant the number of data taken at one time. The values of the two peaks are compared in threshold comparator 69 to determine their ratio. If the determined brightness ratio exceeds some threshold, predetermined on the basis of experience, the pixel is retained in the signal, otherwise, it is zeroed. This is done for each of the 32 signals, and the result is again a set of 32 signals. The most common parameters for this operator have been found to be: filter width=11 pixels, central width=5 pixels and ratio threshold=1.3.

Figure 12:
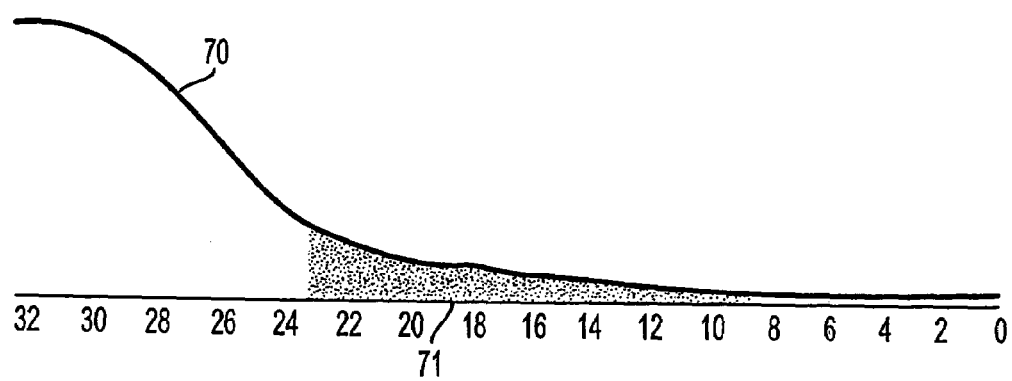

If at least one of the 32 signals produced by a pixel has a high bump, viz. its brightness ratio is above the threshold, all 32 signals relative to said pixel are passed on to this estimator for the statistical evaluation. Therefore, in this embodiment, and optionally in general, bump detection is a first preliminary stage filter performed prior to the vector die-to-die comparison. However, the number of signals relative to each pixel that have a brightness ratio above the threshold (the output of bump detection) gives an indication as to whether the pixel is likely to be considered suspect. For instance, a single signal having a high bump may be due to the wafer pattern, whereas a high number of such signals is probably due to a particle. The decay rate estimator 68 (see FIG. 10) analyzes the 32 signals relative to each pixel (the output of bump detection) and provides some statistical indicator of their values. Therefore, in this embodiment, and optionally in general, decay rate estimation is a second preliminary stage of the vector die-to-die comparison, successive to bump detection. The algorithm uses three parameters: central value percentile p, width factor w, and threshold s. The computation is as follows: Sort the 32 values. Pick the p percentile value. Sum all values that are between p*w and p/w. The sum is sent to a threshold comparator. The result of the comparator is 1 or 0, according to whether the sum is greater or smaller than s. Common values have been found to be p=w=0.5. The value of s is variable, and has to be empirically determined. This procedure is illustrated by an example in FIG. 12, wherein numeral 70 indicates a curve which interpolates all the percentile values. The area 71 (marked in black) under curve 70, between twice the center value and one half the center value, is compared to an empirical threshold.

Whereas the input to the signal processor unit is synchronous data at the system's clock, the frequency of the output is on the average 2-4 orders of magnitude smaller. A standard interface with some memory is designed into the system to handle potential peaks of activity, and to push the data down a PCI bus to the host computer (e.g. Pentium II by Intel Corporation Limited). Each output suspect feature is built of coordinate data and type data. The coordinate data is provided by the mechano-electronic subsystem in polar coordinates ($\rho$ and $\theta$) and can be translated, using the registration transformation described herein, to wafer coordinates. The type data is in the case of the algorithm detailed above the output of the decay rate estimator (the number that was sent to the threshold comparator). This is an indication of the strength of the detection, or, in other words, of the detection certainty.

The Defect Detection Unit 53 is a software module whose job is to receive the data relative to all the suspect pixels from the previous stage, and find out which of them represent real defects, viz. to carry out the vector die-to-die comparison (VDDC), which follow the preliminary stages of bump detection and decay rate estimation, if these have been carried out. The VDDC operation comprises the following:
1. Transforming the polar coordinates of the machine to the Cartesian coordinates of the die coordinate system.
2. Deriving from the coordinates that define the suspect pixels' location in the machine coordinate system the coordinates that define said location in the die coordinate system.
3. Marking in the die coordinate system the position of all suspect pixels.
4. Discriminating between suspect pixels that are due to the wafer pattern, and therefore do not represent a defect, and suspect pixels that are not due to it and therefore do represent a defect, in particular those deriving from foreign particles.

Figure 13:
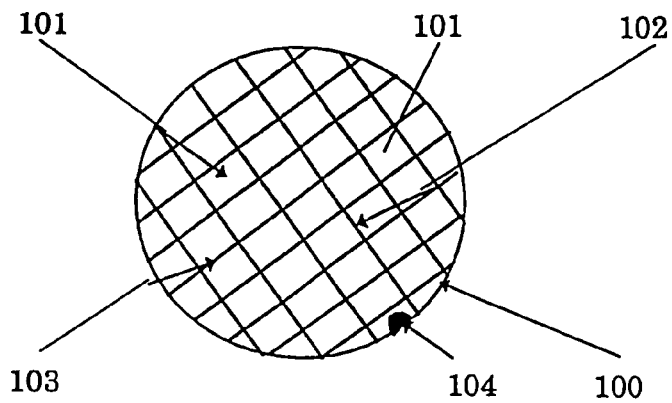
FIG. 13 illustrates the die coordinate system.

FIG. 13 illustrates how the coordinates that define the suspect pixels' location in the die coordinate system are derived from their coordinates in the machine coordinate system. When a new wafer 100 is placed, generally by means of a robot, on the rotary plate of the inspection apparatus of the invention, the orientation of the wafer is unknown and it may be miscentered by up to 1 mm. It is important for the later parts of the inspection procedure, and of course for the output of the list of defective pixels, to be able to describe the location of each pixel on the wafer with the wafer's natural frame of coordinates. The wafer is composed of many identical dies 101, each one of which is destined to constitute (if not faulty) a semiconductor device or part of such a device, such as a CPU or a memory chip. The dies are separated by the scribe lines, along which the wafer will be cut when ready, which form two perpendicular families of lines, that can be called, for convenience of illustration, avenues 102 and streets 103. Avenues and streets, collectively, can be called "the principal directions of the die". The avenues are considered as oriented from "south" to "north" and the streets from "west" to "east". At one point on the circumference of the wafer there is a small recess, called a notch 104, which defines the wafer's "south".

The procedure of defining the wafer map and registering it with reference to the machine coordinate system, is carried out as follows:
1. A short pre-scan is carried out, typically by rotating the machine plate by 100 turns, spanning about 20 mm width of the external circumference of the wafer.
2. The notch is detected by its known, typical signature.
3. Streets and avenue pixels are detected by their specific signatures, which are determined by their being mirror-like in most of their area.
4. The detected notch and street and avenue pixels are transmitted to the CPU that controls the procedure.
5. A registration algorithm receives the said input and computes the angle of rotation of the wafer's coordinate system with respect to the machine's coordinate system, and also the locations of the streets and avenues.

This allows a map of the wafer to be constructed (when a new wafer is introduced) or a registration transformation to be computed (if the map is already known). If the wafer is a bare wafer, then only the notch can be detected and a registration transformation of lower accuracy can be computed, using the location of the notch. Such registration transformation can be carried out by means of known algorithms, e.g. by the randomized Hough transform technique—see L. Xu, E. Oja and P. Kultanen, A new curve detection method, Randomized Hough Transform (RHT), Pattern Recognition Letters, vol. 11. no. 5, May 1990, pp. 331-338, Elsevier Science Publishers B. V. (North-Holland—or by other algorithms easily devised by expert persons.

Figure 18:
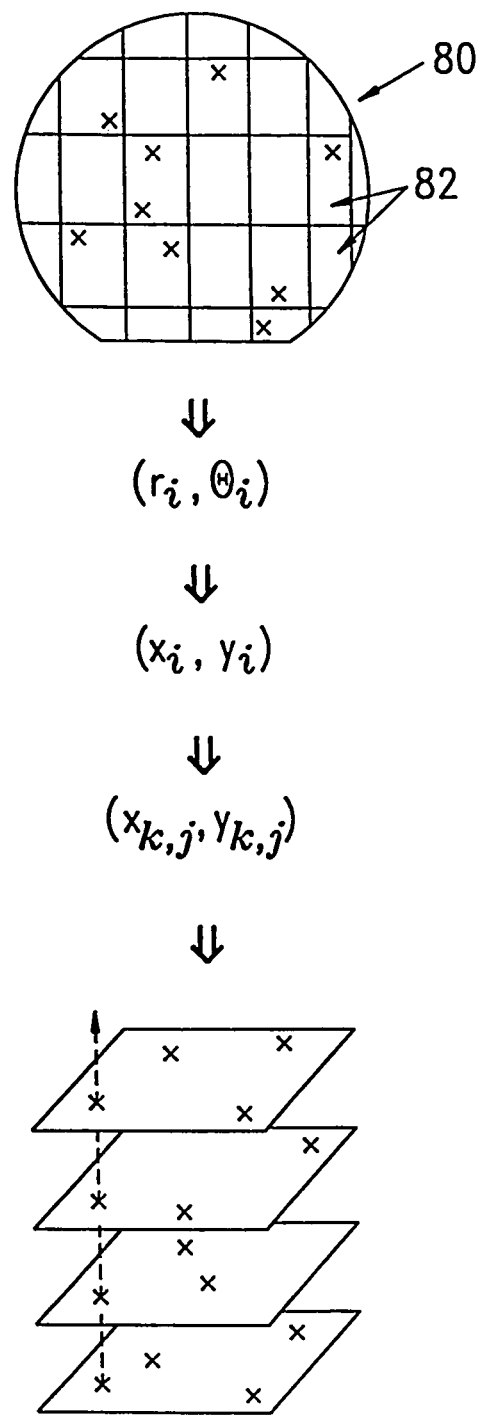
FIG. 18 is a conceptual flow chart exemplifying the vector die-to-die comparison according to the preferred embodiment of the present invention.

The inventive vector die-to-die comparison (VDDC) will now be described. Conceptually, unlike the conventional die-to-die comparison, wherein each $(x_i, y_i)$ location on a die is compared to the corresponding location on the preceding and following die, the VDDC "stacks" all the dies and checks to see whether a suspect $(x_0, y_0)$ location appears in a corresponding location in more than one die. The entire operation, including the coordinates transformation, can be better understood with reference to FIG. 18. FIG. 18 depicts a defect map in the form of a wafer, 80, having a plurality of dies 82 thereon, and having "suspected" defect locations, each marked with an "x".

In the apparatus according to the preferred embodiment, the suspected locations are provided in polar coordinates, i.e., $(r_j, \theta_i)$ pairs. Therefore, the suspected locations' coordinates are first transformed into the cartesian coordinates of the wafer, i.e. $(x_j, y_i)$ pairs, and thence to the cartesian coordinates of the corresponding dies, i.e. $(x_{kj}, y_{kj})$ pairs (k standing for the die and j standing for the coordinate within the die). Once the $(x_{kj}, y_{kj})$ pairs of all the suspected locations within the wafer have been obtained, the dies are "stacked" to see whether any suspect location $(x_{kj}, y_{kj})$ appears in more than one die. Here, much information about the suspect locations can be obtained. For instance, if a particular $(x_{kj}, y_{kj})$ pair appears in all the dies, it is likely to be a feature of the die structure and not a defect.

Also, as is known in the art, the patterns on the wafers are created by a process called photolithography, which uses reticles having the desired pattern thereupon. It is known to use reticles which have, for example, a multiple of four die patterns thereupon. Thus, if during the VDDC it is determined that a particular $(x_{kj}, y_{kj})$ pair appears in every fourth die, it is likely that the defect has been transferred from a defective reticle. Thus, this information can be used to set thresholds and other filtering mechanisms for the VDDC.

As can be seen from the above, using the VDDC discrimination is now effected between two types of suspect data:

a) Suspect data that are actually produced by the wafer pattern, but appear as if they were due to the presence of particles (and therefore are detected as indicating such presence). These will appear in many or all of the dies. Thus, in die coordinates, one will see numerous appearances of suspects at the same location. All the suspects that appear at that location are discarded. It may be advantageous to filter the data in some way before the VDDC, for example by utilizing a method that recognizes that a group of points form together some specific geometric configuration, for example line segments. This group can then be considered as a legitimate pattern of the wafer and filtered out of the set of suspect points. This allows the VDDC to operate on a smaller set of isolated points and thereby to achieve better performance.

b) Suspect data that are produced by real contamination by particles. These appear essentially only once on the, die map.

The detailed construction of software that implements this algorithm is a routine task for a skilled algorithm designer.

It should be appreciated, of course, that rather than using the inventive VDDC, one may choose to perform a conventional die-to-die or cell-to-cell comparison. Even if such an approach is taken, the inventive system reduces processing time, since, unlike conventional die-to-die systems wherein all the pixels are compared to their near neighbors, only the suspect pixels flagged by the Signal Processor Unit 52 need to be compared to their near neighbors. Of course, in such a case, each time the Signal Processor Unit 52 flags a suspect pixel, the near neighbor pixels need to be stored in the memory for the die-to-die comparison.

Figure 14A:
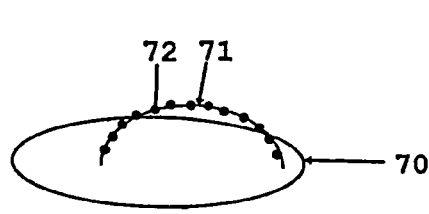
FIGS. 14(a), (b) and (c) and FIG. 15 schematically illustrate alternative dispositions of the scattered radiation collectors.
Figure 14B:
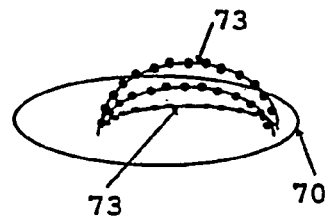
Figure 14C:
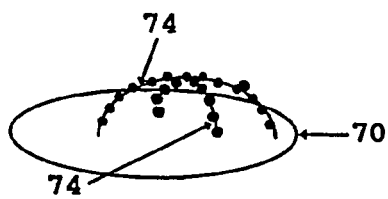

FIGS. 14(*a*), (*b*) and (*c*) schematically illustrate the disposition of scattered radiation detectors above the wafer surface and not peripherally as in the previously described embodiments. The fixed directions, therefore, are elevationally and not azimuthally spaced. The wafer is indicated at 70. In FIG. 14(*a*) only one semicircular detector ring 71 is shown, along which detectors 72 are disposed. Such a ring will detect radiation scattered on a plane perpendicular to the wafer plane, at different elevational angles on said plane. In FIG. 14(*b*) several semicircular rings 73 of detectors are provided, in any desired number, though only three are shown for convenience of illustration in the drawing. The rings are on different planes, differently slanted with respect to the wafer plane. If there is an odd number or rings, the central one will be on a plane perpendicular to the wafer plane. FIG. 14(*c*) shows two rings 74 of detectors, disposed on two planes perpendicular to the wafer plane and perpendicular to each other. In this case too, any desired number of detector rings could be provided. It is clear that the geometric arrangement of the detectors can be changed as desired.

Figure 15:
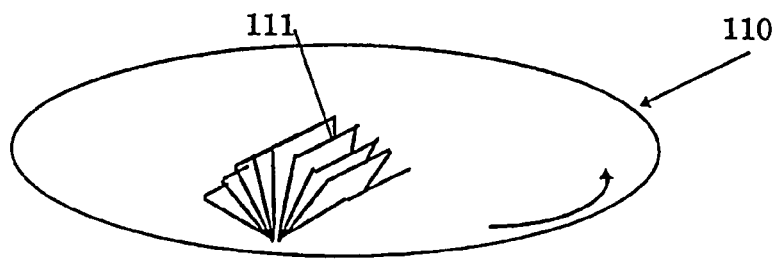

In a further embodiment of the invention, schematically illustrated in FIGS. 5 and 15, pixel signatures are determined by components that are determined by measuring elevation angles scattering rather than azimuthal angles scattering signature. In this case, it is possible and preferable to use line CCD detectors and line laser diode bars placed as a fan. Thus FIG. 15 shows a wafer 110 with a set of linear CCD elements 111. For instance, there can be used CCDs with 1000 detectors each, arranged as a fan with 10 units. One of these elements can be replaced with a laser diode bar. This provides the required illumination, together with the versatility needed to set the illumination angle to suit each particular case. With 1000 detectors, each capturing the energy from a pixel with radial dimension of 15 microns, one would cover 15 mm. of the wafer's radius, that is, about 10%. Therefore an apparatus according to the invention with e.g. 10 static heads could be used in place of an apparatus with one head moving radially across the wafer.

Figure 16:
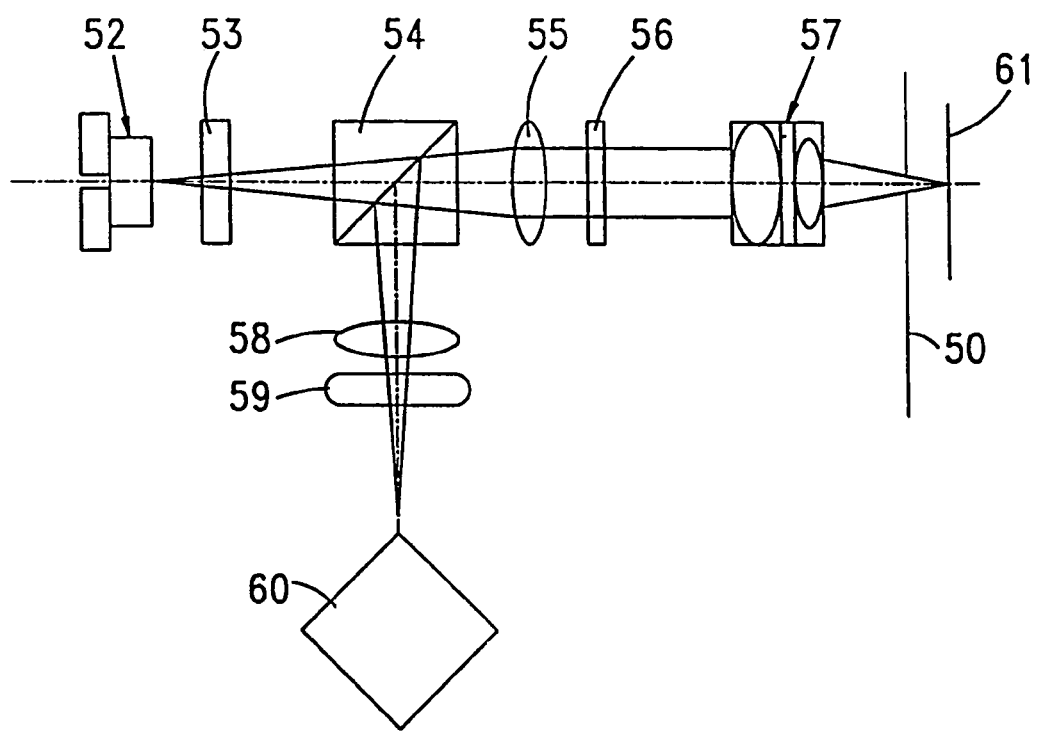
FIGS. 16 and 17(a), (b) and (c) illustrate a method and apparatus for height measurement.
Figure 17A:
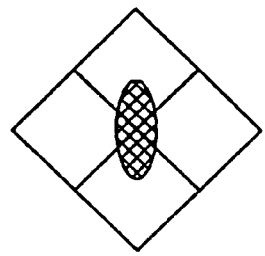
Figure 17B:
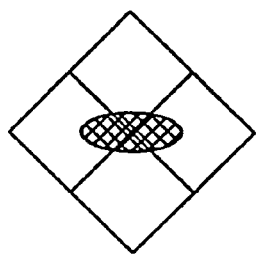
Figure 17C:
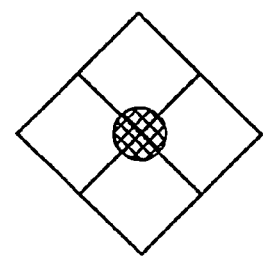

The depth measurement is optional and, when effected, can be carried out by devices known in the art as to themselves, although never before applied to the testing of semiconductor wafers. Such devices are used, e.g. as autofocusing mechanisms in the Compact Disk art. See for example H.D. Wolpert, "Autoranging/Autofocus—A Survey of Systems", Photonics-Spectra, June p.65, August p.127, September pp. 133-42, Vol. 21, Nos. 8 and 9 (1987). Schematically, they may be constituted and operate as illustrated by way of example in FIGS. 16 and 17. In FIG. 16, 50 designated a portion of a patterned wafer surface, on which a large particle may have been deposited. A laser diode 52 emits a beam which enters a diffraction grating 53, which converts the beam into a central peak plus side peaks. The resulting three beams go though a polarizing beam splitter 54, which only transmits polarization parallel to a plane, which in this example is assumed to be the plane of the drawing. The emerging, polarized light is collimated by collimator 55. The collimated light goes through a ¼ wave plate 56. This converts it into circularly polarized light. The circularly polarized light is then focused onto the wafer through objective lens 57. The light reflected by the wafer goes back into the objective lens 57 and then passes once again through the ¼ plate. Since it is going in the reverse direction, it is polarized perpendicularly to the original beam, viz, perpendicularly, in this example, to the plane of the drawing. When the light hits the beam splitter 54 once again, it is reflected through a focusing lens 58 and a cylindrical lens 59 and is imaged on a photodetector array 60. If the objective lens is closer to the reflecting area of the wafer than the focal plane 61 of the objective lens 57, an elliptical image is created on the photodetector array 60, as shown in FIG. 17(*a*). If it is farther away than said focal plane, another elliptical image is created, perpendicular to the first one, as shown in FIG. 17(*b*). If the reflecting area of the wafer is at the focal length of the objective lens, the cylindrical lens does not affect then image, which is circular, as shown in FIG. 17(*c*). Therefore, if the pattern of a wafer produces a circular image, due to the lands of the pattern, viz, the plane of the wafer, being at the focal plane of the objective lens, and when a given pixel is illuminated an elliptical image is formed, this will indicate the presence of a particle the size of which cause it to project above the pattern lands. The displacement signal of the objective lens, required to reestablish a circular image, can give a measure of the amount by which the particle projects above the plane of the wafer.

It should be noted that, while the invention has been described and illustrated on the assumption that the surface to be analyzed is the upper surface of a body, in particular of a wafer, and therefore the irradiating beam is directed downwardly onto it, the supporting shaft is located below it, and in general all parts of the apparatus conform to this geometric orientation, the apparatus could be differently oriented, and, e.g., overturned, so that that the surface to be analyzed be the lower surface of a body, in particular of a wafer, with all the attending structural consequences.

While examples of the method and apparatus of the invention have been described by way of illustration, it will be apparent that the invention may be carried out with many variations, modifications and adaptations by persons skilled in the art, without departing from its spirit or exceeding the scope of the claims.

The invention claimed is:

1. A method of inspecting a patterned wafer for defects, the method comprising:
    illuminating the wafer with a pulsating laser;
    establishing relative motion between the wafer and the pulsating laser;
    acquiring first scattered light from a first area of the wafer with a first detector array;
    acquiring second scattered light from a second area of the wafer with a second detector array, the first area of the wafer being at least partially different than the second area of the wafer, the first scattered light being at least partially different than the second scattered light, the first detector array acquiring the first scattered light concurrently with the second detector array acquiring the second scattered light; and
    applying a die-to-die comparison method to detect defects, wherein said die-to-die comparison method is a vector die-to-die comparison method.

2. The method according to claim 1, said pulsating laser having an ultraviolet wavelength.

3. The method according to claim 1, said first and second detector arrays being CCD detector arrays.

4. The method according to claim 1, said first and second detector arrays each being one of multiple detector arrays.

5. A method of inspecting a patterned wafer for defects, the method comprising:
    illuminating the wafer with a pulsating laser;
    establishing relative motion between the wafer and the pulsating laser;
    acquiring scattered light from the wafer with a plurality of CCD detector arrays, each of the CCD detector arrays concurrently acquiring at least partially different portions of light scattered from adjacent and at least partially different areas of the wafer; and
    applying a die-to-die comparison method to detect defects, wherein said die-to-die comparison method is a vector die-to-die comparison method.

6. The method according to claim 5, said pulsating laser having an ultraviolet wavelength.

7. The method according to claim 5, said pulsating laser being one of a plurality of lasers.

8. A method for inspecting a patterned wafer, the method comprising:
    illuminating the wafer with at least one pulsating light source;
    establishing relative motion between the wafer and the light source;
    acquiring scattered light from the wafer with a plurality of detector arrays, each of the detector arrays concurrently acquiring at least partially different portions of scattered light from at least partially different areas of the wafer; and
    applying a die-to-die comparison method to detect defects, wherein said die-to-die comparison method is a vector die-to-die comparison method.

9. The method according to claim 8, said plurality of detectors arrays each comprising a CCD detector array.

10. The method according to claim 8, wherein the acquired scattered light is collected at a plurality of points of light collection.

11. The method according to claim 10, wherein the points of light collection are parallel to the wafer.

12. The method according to claim 8, wherein the different areas of the wafer overlap.

13. The method according to claim 8, said establishing relative motion between the wafer and the light source comprising moving the wafer during the illuminating.

14. A method of inspecting a patterned wafer, the method comprising:
    illuminating the wafer with at least one pulsating light source such that a plurality of different areas of the wafer are concurrently illuminated;
    concurrently acquiring scattered light from at least partially different areas of the wafer with a plurality of detector arrays, each of the detector arrays acquiring different portions of the scattered light that correspond to the different areas of the wafer; and
    detecting defects by a comparison methods,
    wherein said comparison method is a vector die-to-die comparison method.

15. The method according to claim 14, wherein the plurality of detectors arrays each comprise a CCD detector array.

16. The method according to claim 15, further comprising: establishing relative motion between the wafer and said at least one pulsating light source.

17. The method according to claim 16, wherein the acquired scattered light is collected at a plurality of points of light collection.

18. The method according to claim 16, wherein the at least partially different areas of the wafer overlap.

19. A method of improving throughput when inspecting a patterned wafer for defects, the method comprising:
    concurrently illuminating at least partially different areas of the wafer with a pulse of at least one laser; and
    concurrently acquiring scattered light from the wafer with a plurality of CCD detector arrays, each of the CCD detector arrays concurrently acquiring at least partially different portions of light scattered from different ones of the different areas of the wafer so as to improve throughput by detecting defects during a die-to-die inspection method relying on vector die-to-die comparison.

20. A system for inspecting a patterned wafer for defects, the system comprising:
    a pulsed laser for illuminating the wafer;
    a stage that provides relative motion between the wafer and the laser;
    an optical assembly having a first detector array and a second detector array, the first detector array for acquiring first scattered light from a first area of the wafer, the second detector array for acquiring second scattered light from a second area of the wafer, the first area of the wafer being at least partially different than the second area of the wafer, the first scattered light being at least partially different than the second scattered light, the optical assembly being configured such that the first detector array acquires the first scattered light concurrently with the second detector array acquiring the second scattered light; and a processor that applies a die-to-die comparison method to detect defects, wherein said die-to-die comparison method is a vector die-to-die comparison method.

21. The system according to claim 20, said pulsed laser having an ultraviolet wavelength.

22. The system according to claim 20, said first and second detector arrays being CCD detector arrays.

23. The system according to claim 20, said first and second detector arrays each being one of multiple detector arrays.

24. A system for inspecting a patterned wafer for defects, the system comprising:

a pulsed laser;

a stage that provides relative motion between the wafer and the laser;

a plurality of CCD detector arrays for acquiring scattered light from the wafer, each of the CCD detector arrays concurrently acquiring at least partially different portions of light scattered from adjacent and at least partially different areas of the wafer; and a processor that applies a die-to-die comparison method to detect defects, said die-to-die comparison method being a vector die-to-die comparison method.

25. The system according to claim 24, said laser having an ultraviolet wavelength.

26. The system according to claim 24, said laser being one of a plurality of lasers.

27. A system for inspecting a patterned wafer, the system comprising:

at least one pulsed light source;

means for establishing relative motion between the wafer and the light source;

a plurality of detector arrays for acquiring scattered light from the wafer, each of the detector arrays being configured to concurrently acquire at least partially different portions of scattered light from at least partially different areas of the wafer; and means for applying a vector die-to-die comparison method to detect defects.

28. The system according to claim 27, said plurality of detectors arrays each comprising a CCD detector array.

29. The system according to claim 27, wherein the different areas of the wafer overlap.

30. A system of inspecting a patterned wafer, the system comprising:

at least one pulsating light source that concurrently illuminates a plurality of different areas of the wafer;

a plurality of detector arrays configured to concurrently acquire scattered light from at least partially different areas of the wafer, each of the detector arrays acquiring different portions of the scattered light that correspond to the different areas of the wafer; and a processor that detects defects by a comparison method, wherein said comparison method is a vector die-to-die comparison method.

31. The system according to claim 30, wherein the plurality of detectors arrays each comprise a CCD detector array.

32. The system according to claim 31, further comprising:

a stage that establishes relative motion between the wafer and said at least one pulsating light source.

33. The system according to claim 30, wherein the at least partially different areas of the wafer overlap.

34. A system for inspecting a patterned wafer, the system comprising:

at least one pulsed laser having a footprint that concurrently illuminates at least partially different areas of the wafer;

an optical assembly comprising a plurality of CCD detector arrays each arranged to concurrently acquire at least partially different portions of light scattered from different ones of the different areas of the wafer, and a processor for detecting defects by a vector die-to-die comparison method.

35. The system according to claim 34, further comprising: at least one polarizer for polarizing the scattered light.

* * * * *